United States Patent [19]

Cooper

[11] Patent Number: 4,890,936

[45] Date of Patent: Jan. 2, 1990

[54] WASTE BAG

[75] Inventor: Christopher Cooper, London, England

[73] Assignee: Guardine Disposable Limited, Hemel Hempstead, Great Britain

[21] Appl. No.: 189,941

[22] Filed: May 3, 1988

[30] Foreign Application Priority Data

Nov. 20, 1987 [GB] United Kingdom ................. 8727228

[51] Int. Cl.⁴ ............................................ B65D 30/08
[52] U.S. Cl. .................................... 383/109; 383/113; 383/114; 383/116
[58] Field of Search ................. 383/70, 109, 113, 114, 383/116

[56] References Cited

U.S. PATENT DOCUMENTS

| | | | |
|---|---|---|---|
| 893,759 | 7/1908 | Thomas | 383/113 X |
| 2,667,198 | 1/1954 | Klein | 383/110 X |
| 3,485,281 | 12/1969 | Wicks | 383/109 |
| 3,570,748 | 3/1971 | Coyle | 383/116 |
| 4,401,256 | 8/1983 | Kries | 383/116 |
| 4,735,308 | 4/1988 | Barnes | 383/113 X |

FOREIGN PATENT DOCUMENTS 0217667 4/1987 European Pat. Off. ............ 383/113

OTHER PUBLICATIONS

Gary Falkenstein, Packaging Reference Issue, 1986, pp. 50–52.

Primary Examiner—Stephen Marcus
Assistant Examiner—Nova Stucker
Attorney, Agent, or Firm—Berman, Aisenberg & Platt

[57] ABSTRACT

A waste bag made of a synthetic plastics material. It has an internal lining of a liquid-absorbent material which terminates inwardly of the mouth of the bag, so that the latter is free of lining in the region of its mouth to enable that region to be gathered and tied.

8 Claims, 1 Drawing Sheet

WASTE BAG

The present invention relates to a waste bag.

Various kinds of waste material which have to be disposed of can comprise fluids and objects with corners or relatively sharp edges. If such waste material is put in a waste bag, there is a risk that the corners or relatively shaped edges will puncture the wall of the bag, and that the fluids may then leak out.

One particularly dangerous situation in which waste is disposed of in bags arises in hospitals. Clinical waste is often disposed of along with relatively hard surgical or clinical articles. The risk of a leak of blood from such a bag is particularly dangerous, as the blood may be contaminated with the hepatitis or HIV virus. Infection has already been known to occur in this way, particularly during perfusion after which pipe fittings, intercoolers, and oxygenaters containing up to half a liter of blood are dropped into a waste bag which is then gathered at its top and sealed with wire, tape, or other tie. Up to twelve bags have been placed one inside the other hitherto, to reduce the risk of a tear occurring.

The present invention aims to reduce the liklihood of a tear occurring in the disposal of waste material in a bag, preferably so as to reduce the hazard of infection from contaminated blood in the disposal of clinical waste, whilst providing a bag which is as readily loaded and tied as a conventional waste bag.

Accordingly the present invention is directed to a waste bag made of a synthetic plastics material and having an internal lining of a liquid-absorbent material which terminates inwardly of the mouth of the bag, so that the latter is free of lining in the region of its mouth to enable that region to be gathered and tied.

Such a waste bag may comprise a co-extruded triple laminate of polyamide sandwiched between polyethylene. This combines the advantages of a polyamide, for example nylon, which is a good gas barrier and therefore prevents odours escaping the bag, and polyethylene, which is readily heat sealed to itself and to the lining. A cheaper laminate would be a twin laminate, comprising a layer of polyamide and a layer of polyethylene, in which case the polyethylene would be arranged on the inside, against the lining, so that its heat sealing properties can be used effectively. The lining may comprise a non woven material, for example a non woven polyamide.

A second aspect of the present invention is directed to a waste bag made of a co-extruded triple laminate comprising a polyamide sandwiched between polyethylene, in which the polyamide constitutes a proportion substantially in the range from 15% to 25% of the laminate by weight and in which the laminate has a thickness substantially in the range from 80 to 120 microns. Such a bag provides the advantage of sufficient strength against tearing with sufficient pliability to enable the top of the bag to be gathered into a neck portion and held by a tape, wire, or other tie without the flutes so formed providing any passageways through which blood or other fluid can seep out by gravitational flow, capillary flow, or by wick action.

A third aspect of the present invention is directed to a waste bag having a lining which is doubled back on itself at the bottom of the bag so that the lining is continuous thereat.

This affords the advantage that a good resistance to tearing is formed at the bottom of the bag when a heavy or sharp object is dropped into it.

An example of a bag made in accordance with the present invention is illustrated in the accompanying drawing in which.

Figure 1:
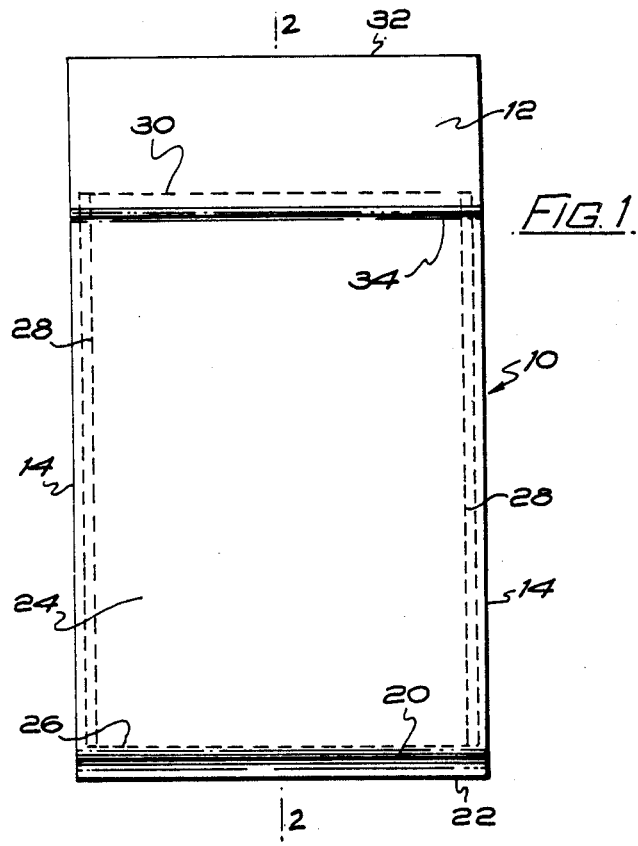
FIG. 1 shows a front of the bag.
Figure 2:
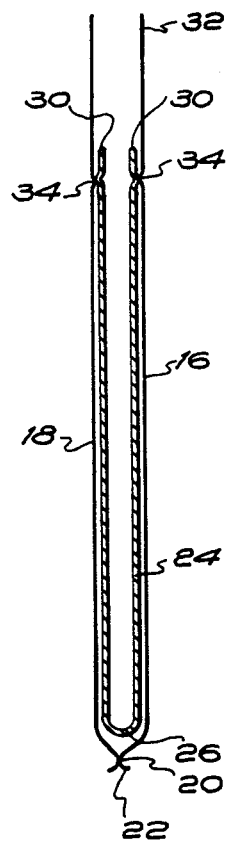
FIG. 2 shows a section of the bag taken along the line II—II in FIG. 1, with the horizontal scale being enlarged for the sake of clarity.

FIGS. 1 and 2 show a clinical-waste bag 10 comprising a co-extruded triple laminate 12. The bag 10 is about 600 mm wide by 1,100 mm in length. The laminate is substantially 100 micron in thickness and comprises polyamide sandwiched between low density polyethylene. Each layer of the polyethylene constitutes 40% by weight of the laminate and the polyamide constitutes 20% by weight of the laminate. One laminate which conforms to this specification is called VYNATECH (TM) made by Vynatech Limited of Farnborough, Hampshire. The laminate is in the form of a section of tubing being the form in which it is blown during the extrusion process, and is laid flat so that it has edges 14. The bag is therefore seamless.

The two sides 16 and 18 of the bag are heat sealed along a fusion line 20 which is slightly spaced from the bottom of the bag 22.

The bag 10 has a lining 24 comprising a non-woven polyamide material made from a sheet thereof which is substantially 0.7 mm thick. One material which conforms to this specification is called CAMBRELLE (TM) made by Camtex Fabrics Limited, of Workington, Cumbria, a subsidiary company of I.C.I. The lining is made from a single sheet folded double along a line 26 which constitutes the bottom of the lining and which is stitched along lines 28 close to its side edges to form a bag which fits inside the laminate 12. The top edge 30 of the lining is about 30 cms from the top edge or mouth 32 of the bag 10. Thus the lining 24 terminates inwardly of the mouth of the bag 10, so that the latter is free of lining in the region of its mouth to enable that region to be gathered and tied.

The laminate 12 and the lining 24 are heat sealed to one another along a fusion line 34 on both sides of the bag just below the top edge of the lining 24.

The laminate is preferably coloured yellow by means of a yellow polymer dye, and has black biohazard markings on its exterior.

Figure 3:
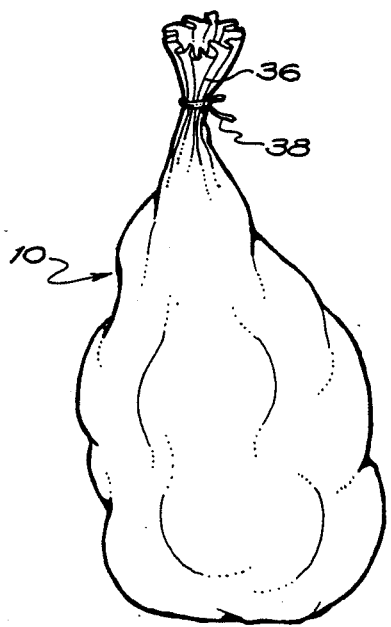
FIG. 3 shows a perspective view of the bag in the closed condition.

When the bag is used, waste is dropped into it, and the upper end thereof is gathered into a neck portion 36 which is held tight by a tape, wire, or other tie 38 as shown in FIG. 3.

A combination of the lining and laminate is resistant to tearing by being stretched or urged against a sharp corner or edge. Furthermore, the lining is absorbent, and in the unlikely event that a puncture of the bag wall does occur, there is unlikely to be excessive seepage of fluid owing to the absorbancy of the lining. For example, up to 90% of a half liter of blood in the bag may be readily absorbed by the lining.

Instead of Cambrelle, the lining could be made from a material called COROVIN, which is spun bonded polypropylene.

In the illustrated bag, the use of the triple laminate on the outside of the bag and a non woven polyamide for the inner lining provides a combination of materials that was difficult to find, in that the overall resulting strength of the bag is high, the absorbancy of the lining is high, the resistance to tearing of both inner and outer bags is high, and the outer layer can be heat sealed to itself and also to the lining. Nonetheless, a waste bag would still provide advantages over those used hitherto, and would still fall within the terms of the present invention, were it made, for example, of tough polythene lined with a liquid-absorbent material.

The lining 24 may be dipped into a disinfectant or antiseptic solution prior to insertion into the laminate 12 during manufacture of the bag. Alternatively, the disinfectant or antiseptic may be coloured, and used as a dye in printing a repeated pattern or logo across the bag.

I claim:

1. A waste bag made of a synthetic thermoplastic plastics material and having an inner bag made of a liquid-absorbent material which constitutes an internal lining of the waste bag, in which the mouth of the inner bag is spaced from the mouth of the waste bag, so that the internal lining terminates inwardly of the mouth of the waste bag and so that the latter is free of lining in the region of its mouth to enable that region to be gathered and tied, and in which the mouth of the inner bag is heat sealed to the synthetic thermoplastic plastics material of the waste bag.

2. A waste bag according to claim 1, wherein the synthetic plastics material comprises a co-extruded triple laminate of polyamide sandwiched between polyethylene.

3. A waste bag according to claim 2, wherein the polyamide constitutes a proportion substantially in the range from 15% to 25% of the laminate by weight and in which the laminate has a thickness substantially in the range from 80 to 120 microns.

4. A waste bag according to claim 1, wherein said lining comprises a non woven material.

5. A waste bag according to claim 4, wherein said lining comprises a non woven polyamide.

6. A waste bag according to claim 1, wherein said lining is doubled back on itself at the bottom of the bag so that said lining is continuous thereat.

7. A waste bag made of a co-extruded triple laminate of polyamide sandwiched between polyethylene, and having an inner bag made of a non woven polyamide liquid-absorbent material which constitutes an internal lining of the waste bag and which is doubled back on itself at the bottom of the bag so that said lining is continuous thereat, in which the mouth of the inner bag is spaced from the mouth of the waste bag, so that the internal lining terminates inwardly of the mouth of the waste bag and so that the letter is free of lining in the region of its mouth to enable that region to be gathered and tied, and in which the mouth of the inner bag is heat sealed to the co-extruded triple laminate of the waste bag.

8. A waste bag made of a co-extruded triple laminate of polyamide sandwiched between polyethylene, in which the polyamide constitutes a proportion substantially in the range from 15% to 25% of the laminate by weight and in which the laminate has a thickness substantially in the range from 80 to 120 microns, the waste bag having an inner bag made of a non woven polyamide liquid-absorbent material which constitutes an internal lining of the waste bag and which is doubled back on itself at the bottom of the bag so that said lining is continuous thereat, in which the mouth of the inner bag is spaced from the mouth of the waste bag, so that the internal lining terminates inwardly of the mouth of the waste bag and so that the latter is free of lining in the region of its mouth to enable that region to be gathered and tied, and in which the mouth of the inner bag is heat sealed to the co-extruded triple laminate of the waste bag.

* * * * *